United States Patent
Ouchi et al.

(10) Patent No.: US 8,257,270 B2
(45) Date of Patent: Sep. 4, 2012

(54) PULSE WAVE MEASURING APPARATUS AND METHOD FOR MEASURING A PULSE WAVE

(75) Inventors: Kazushige Ouchi, Saitama (JP); Takuji Suzuki, Yokohama (JP); Kenichi Kameyama, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 817 days.

(21) Appl. No.: 12/408,855

(22) Filed: Mar. 23, 2009

(65) Prior Publication Data

US 2009/0247886 A1    Oct. 1, 2009

(30) Foreign Application Priority Data

Mar. 25, 2008 (JP) ................ P2008-079230

(51) Int. Cl.
*A61B 5/02* (2006.01)
(52) U.S. Cl. ............ 600/502; 600/500
(58) Field of Classification Search .......... 600/336, 600/481, 500–503; 702/66–80
See application file for complete search history.

(56) References Cited

U.S. PATENT DOCUMENTS

| | | | | |
|---|---|---|---|---|
| 4,793,360 | A * | 12/1988 | Miyawaki et al. | 600/494 |
| 5,140,991 | A * | 8/1992 | Niwa | 600/500 |
| 5,406,952 | A * | 4/1995 | Barnes et al. | 600/485 |
| 5,704,363 | A * | 1/1998 | Amano | 600/500 |
| 6,120,441 | A * | 9/2000 | Griebel | 600/300 |
| 6,361,501 | B1 * | 3/2002 | Amano et al. | 600/500 |
| 7,727,158 | B2 * | 6/2010 | Kitajima et al. | 600/500 |
| 2004/0210145 | A1 * | 10/2004 | Satoh et al. | 600/500 |
| 2005/0234314 | A1 * | 10/2005 | Suzuki et al. | 600/301 |
| 2006/0224074 | A1 * | 10/2006 | Ouchi et al. | 600/513 |
| 2008/0242956 | A1 | 10/2008 | Suzuki et al. | |
| 2009/0018408 | A1 * | 1/2009 | Ouchi et al. | 600/301 |
| 2009/0024014 | A1 * | 1/2009 | Sugo et al. | 600/324 |
| 2009/0076399 | A1 * | 3/2009 | Arbel et al. | 600/500 |
| 2009/0204011 | A1 | 8/2009 | Suzuki | |
| 2009/0281435 | A1 * | 11/2009 | Ahmed et al. | 600/502 |

FOREIGN PATENT DOCUMENTS

| JP | 2003-169780 | 6/2003 |
|---|---|---|
| JP | 2005-279113 | 10/2005 |

* cited by examiner

*Primary Examiner* — Michael Kahelin
*Assistant Examiner* — Meredith Weare
(74) *Attorney, Agent, or Firm* — Turocy & Watson, LLP (57) ABSTRACT

A pulse wave measuring apparatus includes a pulse wave measuring unit measuring a pulse wave; a first detection unit detecting first maximum and minimum values; a second detection unit detecting second maximum and minimum values; an update unit updating the first maximum and minimum values with the second maximum and minimum values after time periods; an initialization unit initializing the second maximum and minimum values after updating the first maximum and minimum values; a timing detection unit detecting a time determined by the first maximum and minimum values; and an interval calculation unit calculating a pulse wave interval using the timing.

10 Claims, 10 Drawing Sheets

PULSE WAVE MEASURING APPARATUS AND METHOD FOR MEASURING A PULSE WAVE

CROSS REFERENCE TO RELATED APPLICATIONS AND INCORPORATED BY REFERENCE

The application is based upon and claims the benefit of priority from the prior Japanese Patent Applications No. JP2008-079230, filed on Mar. 25, 2008; the entire contents of which are incorporated herein by reference.

BACKGROUND OF THE INVENTION

1. Field of the Invention

The present invention relates to a pulse wave measuring apparatus, which is attached to a human body for measuring a pulse wave, and a method for measuring a pulse wave thereof.

2. Description of the Related Art

As an apparatus attached to the human body, such as the wrist, to measure biometric information of a user, an optical pulse wave measuring apparatus is known for measuring a pulse wave.

A pulse wave is generated when blood pressure changes. The pressure change is caused by contraction of the heart, and propagates to peripheral blood vessels. The pulse wave is caused mainly by a change of a flow rate of arterial blood flow. Since an amount of hemoglobin in the blood at a measurement location also changes similar to the flow rate of the arterial blood, it is possible to measure the pulse wave by knowing the amount of hemoglobin at a measurement location.

As one of the methods for measuring the pulse wave, a photoelectric pulse wave method is known. Light absorptivity of the hemoglobin changes depending on the wavelength of light. In the photoelectric pulse wave method, light in a wavelength band covering visible light to near infrared light, which is absorbed by the hemoglobin, is irradiated from a light-emitting element such as a light-emitting diode (LED), and the pulse wave can be known by detecting intensity variations of reflected light or transmitted light, which follows a change of blood flow, with a light-receiving element such as a photodiode.

The blood flow change in an arteriole near the skin can be known by the photoelectric pulse wave measurement method, depending on the wavelength band. Therefore, it is appropriate to conduct the measurement at a location such as the finger; the palm and the earlobe, where a large number of arterioles exist (JP-A 2003-169780).

An apparatus for measuring the pulse wave without burdening the daily life of the user is known (refer to JP-A 2005-279113 (KOKAI)). The apparatus body is put on the wrist like a wrist watch. Only a portion of a pulse wave sensor is removed from the body by a cable and wound around the finger. The pulse wave measurement is taken on a portion of a user's palm. In addition, a pulse wave interval is detected and used to learn some of the physical condition of the user. This invention enhances accuracy of a temporal resolution while sampling the pulse wave at a low speed in order to decrease power consumption. However, in this method, it is necessary to hold all data in a predetermined section of the body of the apparatus since a threshold value for use in detecting the pulse wave is calculated from a maximum and minimum value stored in the section. In order to provide a pulse wave measuring apparatus that does not put a burden on the user, it is necessary to use a microprocessor (MPU) that is compact and energy efficient. However, such a MPU has a restricted capacity RAM. Specifically, a large amount of RAM is used to detect the pulse wave interval. Thus, the useable memory capacity for other functions is decreased, which increases the possibility and decreases a degree of freedom in developing an application.

As described above, heretofore, it has been difficult to calculate a highly accurate pulse wave interval while reserving the memory necessary for pulse wave interval detection processing.

SUMMARY OF THE INVENTION

An object of the present invention is to provide a pulse wave measuring apparatus and a pulse wave measuring method, which can highly accurately calculate a pulse wave interval while saving (retaining) the memory necessary for pulse wave interval detection processing.

An aspect of the present invention inheres in a pulse wave measuring apparatus including: a pulse wave measuring unit configured to measure pulse wave data; a first detection unit configured to detect first maximum values and first minimum values from the pulse wave data, and store the first maximum values and the first minimum values in a first value storage unit, respectively; a second detection unit configured to detect second maximum values, each of which is the next largest value to the first maximum values, and second minimum values, each of which is the next smallest to the first minimum value, from the pulse wave data sequentially, and to store the second maximum values and the second minimum values in a second value storage unit; an update unit configured to update the first maximum value stored in the first value storage unit with the second maximum value after elapse of a maximum value update time period after updating the last first maximum value, and to update the first minimum value stored in the first value storage unit with the second minimum value after elapse of a minimum value update time period after updating the last first minimum value; an initialization unit configured to initialize the second value storage unit so that a new second maximum value can be stored in a next cycle of the pulse wave data, in which the last second maximum value is detected, after updating the last first maximum value, and to initialize the second value storage unit so that a new second minimum value can be stored in a next cycle of the pulse wave data, in which the last second minimum value is detected, after updating the last first minimum value; a timing detection unit configured to detect a timing, at which the pulse wave data intersects a threshold value determined by the last first maximum value and the last first minimum value in two continuous cycles; and an interval calculation unit configured to calculate a pulse wave interval using the last timing and the present timing detected by the timing detection unit.

Another aspect of the present invention inheres in a method for measuring a pulse wave including: detecting first maximum values and first minimum values from data of the pulse wave, respectively and sequentially, and storing the first maximum values and the first minimum values in a first value storage unit; detecting second maximum value, each of which is the next largest to the first maximum values, and second minimum values, each of which is the next smallest to the first minimum values, from the pulse wave data, and storing the second maximum values and the second minimum values to a first value storage unit, respectively; updating the first maximum value stored in the first value storage unit with the second maximum value after a maximum value update time period has elapsed after updating the last first maximum value; updating the first minimum value stored in the first value storage unit with the second minimum value after a minimum value update time period has elapsed after updating the last first minimum value; initializing the second value storage unit so that a new second maximum value can be stored in the next cycle of the pulse wave data, in which the last second maximum value is detected, after updating the last first maximum value; initializing the second value storage unit so that a new second minimum value can be stored in the next cycle of the pulse wave data, in which the last second minimum value is detected, after updating the last first minimum value; detecting timing, at which the pulse wave data intersects a threshold value determined by using the last first maximum value and the last first minimum value in two continuous cycles; and calculating a pulse wave interval using the last timing and the present timing.

DETAILED DESCRIPTION OF THE INVENTION

Various embodiments of the present invention will be described with reference to the accompanying drawings. It is to be noted that the same or similar reference numerals are applied to the same or similar parts and elements throughout the drawings, and the description of the same or similar parts and elements will be omitted or simplified.

Generally and as it is conventional in the representation of devices, it will be appreciated that the various drawings are not drawn to scale from one figure to another nor inside a given figure, and in particular that the layer thicknesses are arbitrarily drawn for facilitating the reading of the drawings.

In the following descriptions, numerous specific details are set fourth such as specific signal values, etc. to provide a thorough understanding of the present invention. However, it will be obvious to those skilled in the art that the present invention may be practiced without such specific details. In other instances, well-known circuits have been shown in block diagram form in order not to obscure the present invention in unnecessary detail.

(Pulse Wave Measuring Apparatus)

Figure 1:
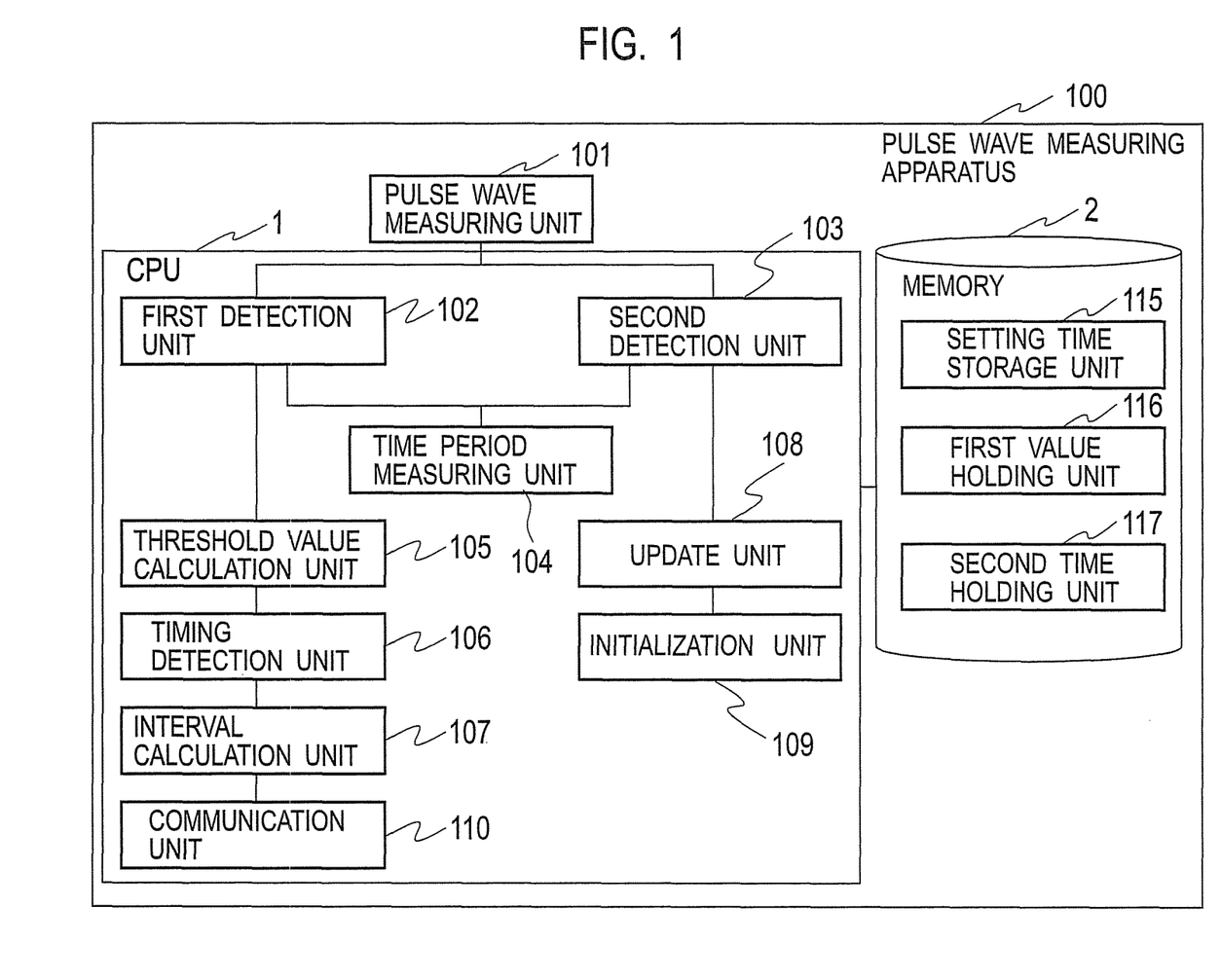
FIG. 1 is a block diagram showing an example of a pulse wave measuring apparatus according to an embodiment of the present invention.

As shown in FIG. 1, a pulse wave measuring apparatus 100 according to an embodiment of the present invention includes a central processing unit (CPU) 1 and a memory 2. The CPU 1 logically includes, as modules (logic circuits) as hardware resources, a pulse wave measuring unit 101; a first detection unit 102; a second detection unit 103; a time period measuring unit 104; a threshold value calculation unit 105; a timing detection unit 106; an interval calculation unit 107; an update unit 108; an initialization unit 109; and a communication unit 110. An input unit, an output device and the like may be connected to the CPU 1 according to needs.

Figure 2:
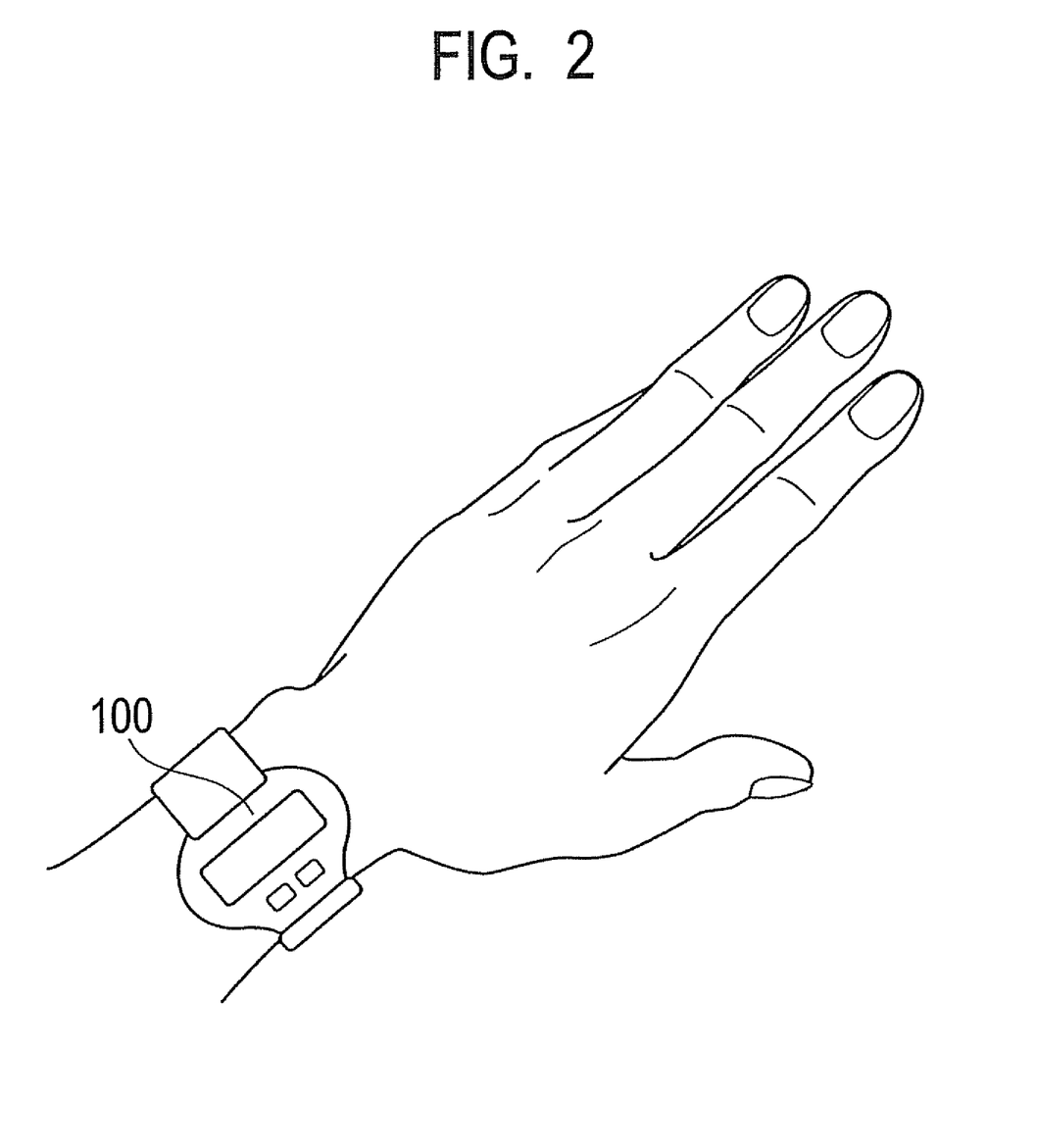
FIGS. 2 to 4 are schematic views showing implementation examples of the pulse wave measuring apparatus according to the embodiment of the present invention.
Figure 3:
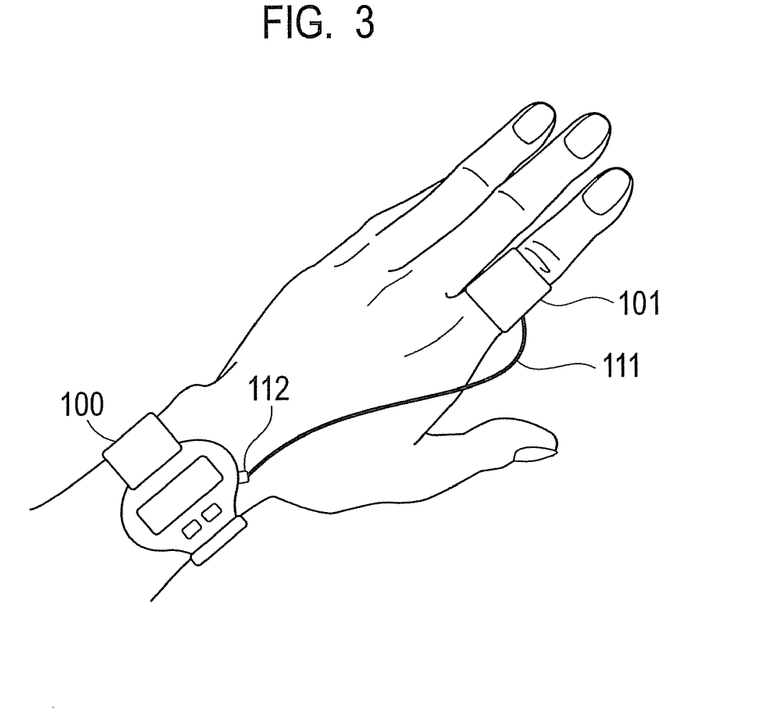
Figure 4:
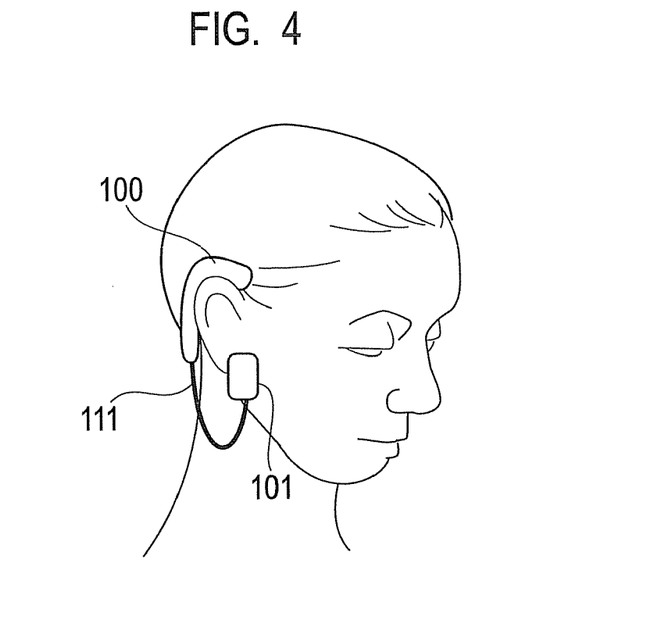
Figure 5:
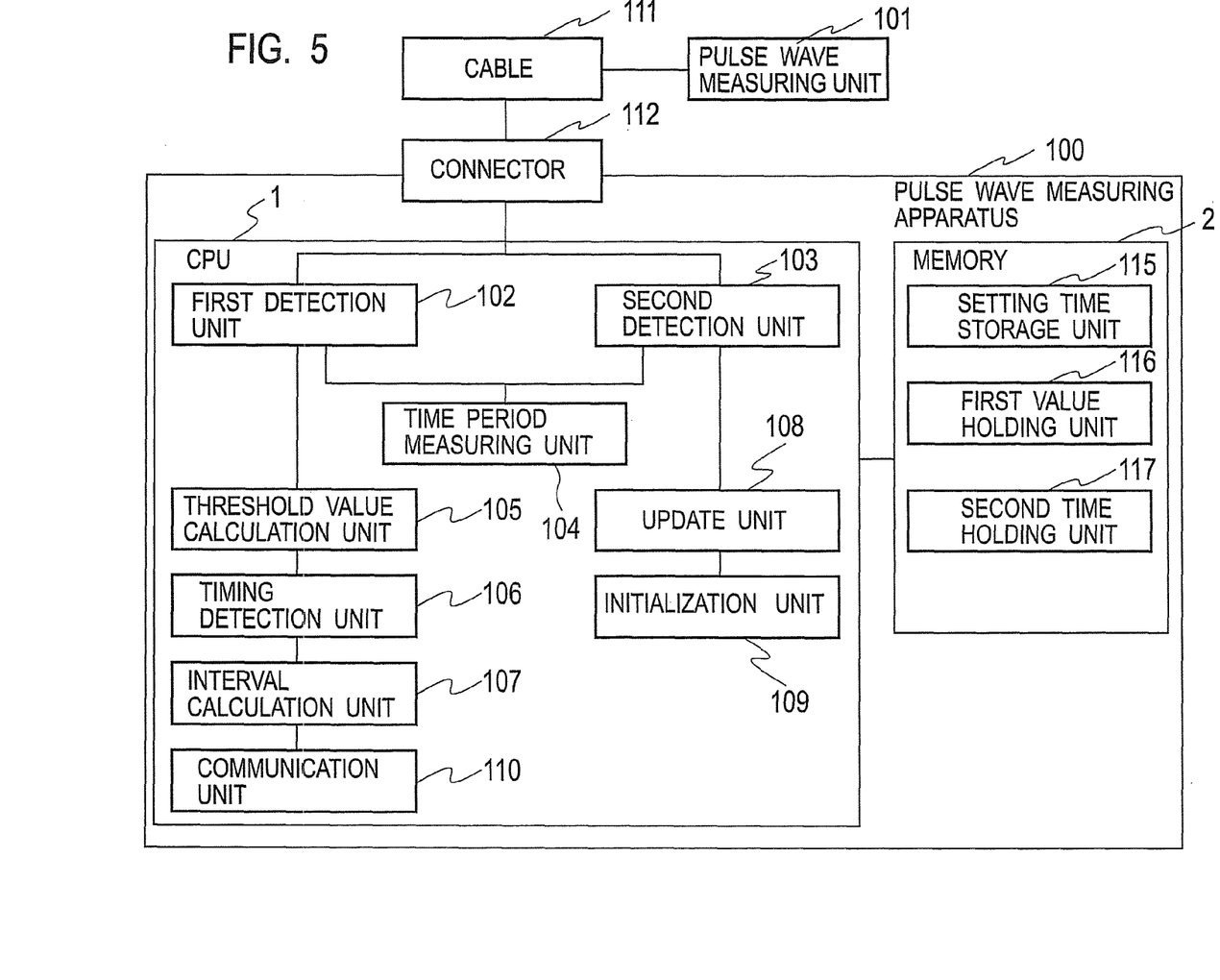
FIG. 5 is a block diagram showing another example of the pulse wave measuring apparatus according to the embodiment of the present invention.

The shape of the pulse wave measuring apparatus 100 is not limited as long as the shape is suitable for measuring a pulse wave. For example, the pulse wave measuring apparatus 100 may be as shown in FIG. 2, which is worn like a wrist watch and measures the pulse wave on the wrist; or as shown in FIG. 3, an apparatus worn like a wrist watch, with the pulse wave measuring unit 101 connected to a finger to measure the pulse wave from a portion of a finger; or as shown in FIG. 4, an apparatus which can be hooked about an ear, and connects the pulse wave measuring unit 101 to the earlobe, to measure the pulse wave. FIG. 5 shows a block diagram of structures such as shown in FIG. 3 and FIG. 4, where the pulse wave measuring unit 101 is located outside (externally) of the pulse wave measuring apparatus 100. The pulse wave measuring unit 101 is connected to the pulse wave measuring apparatus 100 via a cable 111 and a connector 112.

The pulse wave measuring unit 101 measures the pulse wave in every sampling cycle (for example, 50 milliseconds). The pulse wave measuring unit 101 includes a light-emitting element 113 that irradiates, onto a measurement location, light in a wavelength band covering visible light to near infrared light, which is absorbed by hemoglobin; and a light-receiving element 114 that is highly sensitive to the wavelength band of the light irradiated by the light-emitting element 113.

Figure 6:
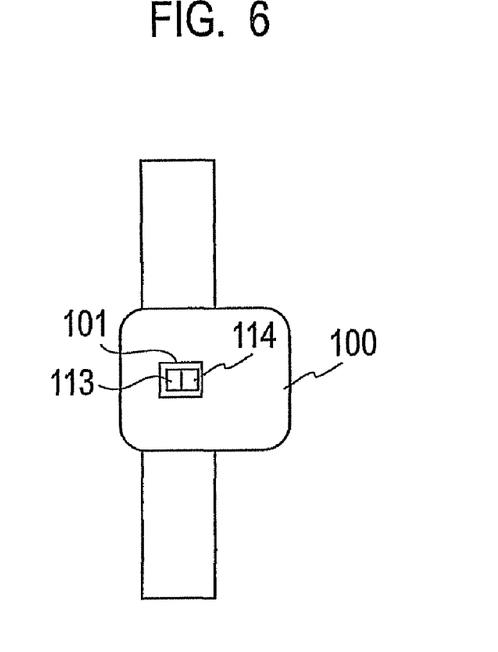
FIGS. 6 and 7 are schematic views showing examples of a pulse wave measuring unit displaced outside of the pulse wave measuring apparatus according to the embodiment of the present invention.
Figure 7:
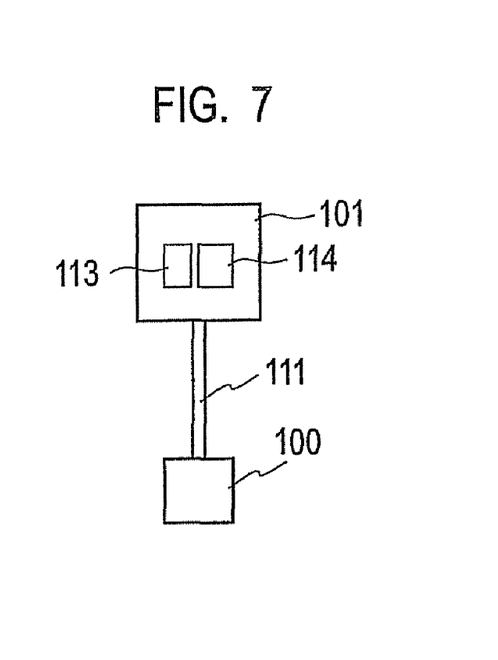

FIG. 6 shows an example where the pulse wave measuring unit 101 is built into the pulse wave measuring apparatus 100, and FIG. 7 shows an example where the pulse wave measuring unit 101 is located outside of the pulse wave measuring apparatus 100. Both of FIGS. 6 and 7 show a configuration example where the light-receiving element 114 receives reflected light of the light irradiated from the light-emitting element 113; however, a configuration may be adopted, in which the light-receiving element 114 receives light transmitted from the irradiated light. The amount of light absorbed by the hemoglobin changes due to a change in blood flow, and accordingly, intensity of the reflected (transmitted) light is changed. The change of intensity is sensed by the light-receiving element 114, whereby the pulse wave can be known. It is desirable that the pulse wave be measured after an output signal from the light-receiving element 114 has been amplified and filtered.

The first detection unit 102 detects a first maximum value from pulse wave data measured by the pulse wave measuring unit 101. The "first maximum value" refers to the maximum value among such pulse wave data for a past predetermined time period (for example, 1.5 second) from the present time.

The first detection unit 102 compares a present value of the pulse wave data measured by the pulse wave measuring unit 101 and the first maximum value stored in a first value holding (storage) unit 116 of the memory 2 with each other, and sequentially detects a present value as a new first maximum value when the present value is larger than a value of the previous first maximum value. As an initial value of the first maximum value stored in the first value holding (storage) unit 116, the minimum value (for example, 0 in the case of performing sampling by a 10-bit A/D converter) among values which the pulse wave can take is set. The value of the first maximum value is sequentially updated. Moreover, the first detection unit 102 detects a first minimum value from the pulse wave data measured by the pulse wave measuring unit 101. The "first minimum value" refers to the minimum value among the pulse wave data for the past predetermined time period (for example, 1.5 second) from the present time. The first detection unit 102 compares the present value of the pulse wave data measured by the pulse wave measuring unit 101 and the first minimum value stored in the first value holding (storage) unit 116 of the memory 2 with each other, and sequentially detects a present value as a new first minimum value when the present value is smaller than a value of the previous first minimum value. As an initial value of the first minimum value stored in the first value holding (storage) unit 116, the maximum value (for example, 1023 in the case of conducting the sampling by the 10-bit A/D converter) among the values which the pulse wave can take is set. The value of the first minimum value is sequentially updated.

Figure 8:
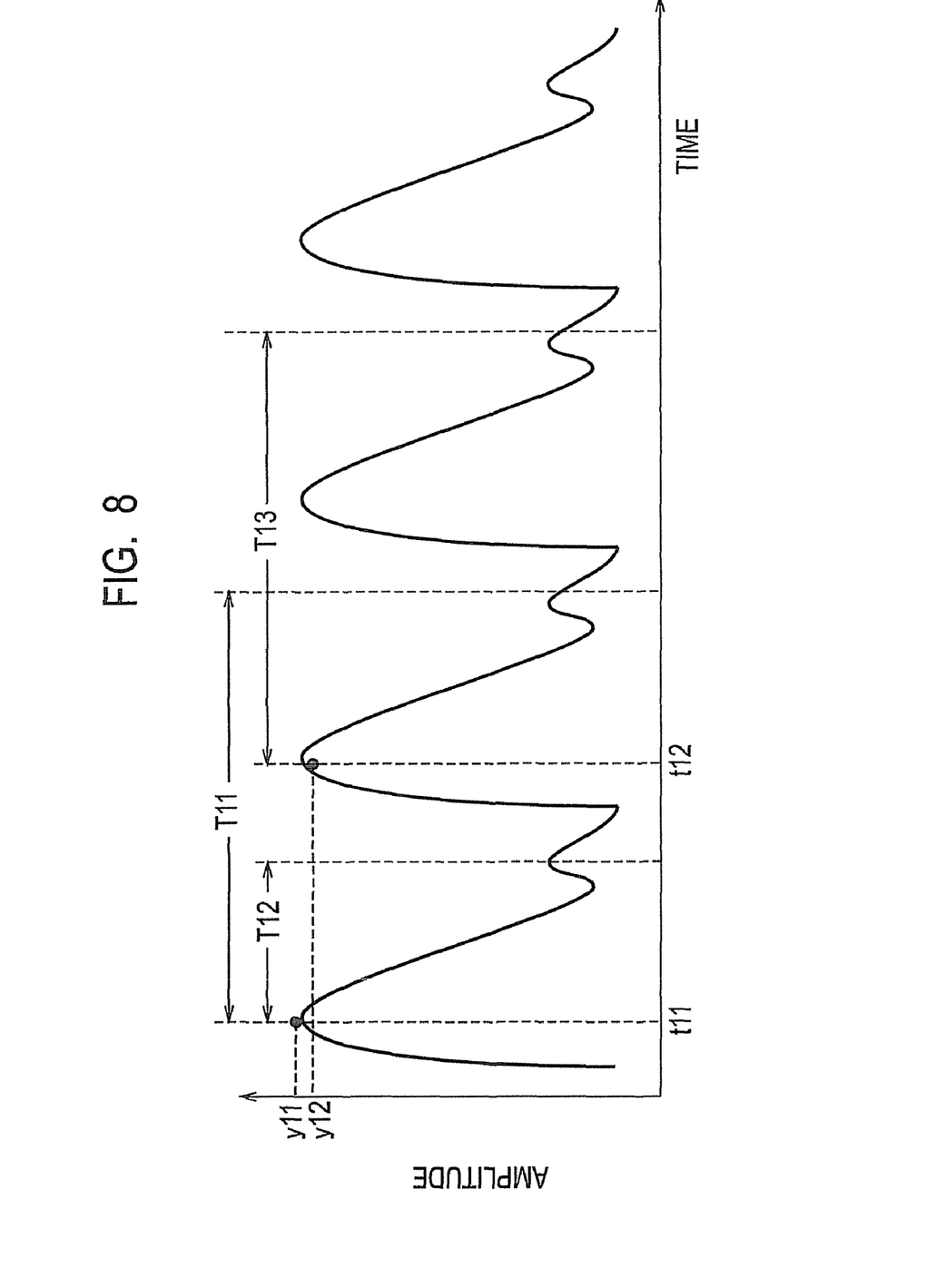
FIG. 8 is a graph for explaining an example of first and second maximum values detection processing in a pulse wave measuring method according to the embodiment of the present invention.
Figure 9:
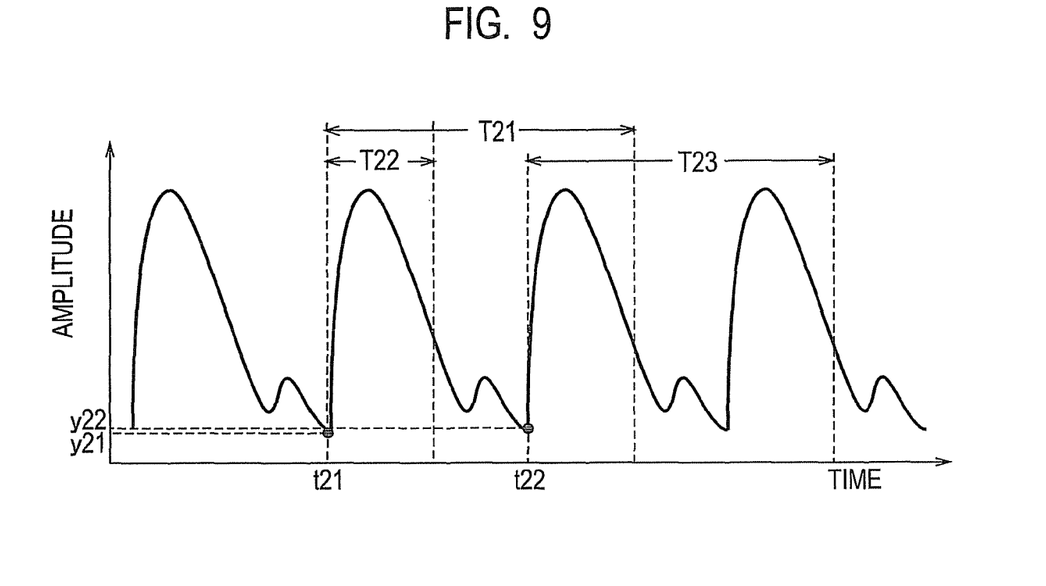
FIG. 9 is a graph for explaining an example of first and second minimum values detection processing in the pulse wave measuring method according to the embodiment of the present invention.

FIGS. 8 and 9 show examples of the pulse wave data. Although the pulse wave data is shown by solid lines, the pulse wave data is actually sampled in every sampling cycle (for example, 50 milliseconds). In FIG. 8, for example, a value y11 of pulse wave data detected at a time t11 is set as the first maximum value. In FIG. 9, for example, a value y21 of pulse wave data detected at a time t21 is set as the first minimum value.

The second detection unit 103 detects a second maximum value from the pulse wave data measured by the pulse wave measuring unit 101. The "second maximum value" refers to the next maximum value after the first maximum value for the past predetermined time period (for example, 1.5 second) from the present time. The second detection unit 103 compares the present value of the pulse wave data measured by the pulse wave measuring unit 101 and the second maximum value stored in a second value holding (storage) unit 117 of the memory 2 with each other, and sequentially detects a present value as a new second maximum value when the present value is smaller than the first maximum value and larger than the second maximum value. As an initial value of the second maximum value stored in the second value holding (storage) unit 117, the minimum value (for example, 0 in the case of performing the sampling by the 10-bit A/D converter) among the values which the pulse wave can take is set. The second maximum value is sequentially updated.

As shown in FIG. 8, the second detection unit 103 starts to detect the second maximum value after a maximum value detection start time period T12 has elapsed from the time t11 when the first detection unit 102 detects the first maximum value y11 or the update unit 108 updates the first maximum value y11. It is recommended that the maximum value detection start time period T12 be set at approximately a half cycle of the assumed pulse wave. The detection of the second maximum value is not started until the maximum value detection start time period T12 elapses. Accordingly, erroneous detection due to the influence of noise, and the like can be eliminated. In FIG. 8, for example, a value y12 of the pulse wave data detected at a time t12 is set as the second maximum value.

Moreover, the second detection unit 103 detects a second minimum value from the pulse wave data measured by the pulse wave measuring unit 101. The "second minimum value" refers to the next minimum value to the first minimum value for the past predetermined time period (for example, 1.5 second) from the present time. The second detection unit 103 compares the present value of the pulse wave data measured by the pulse wave measuring unit 101 and the second minimum value stored in the second value holding (storage) unit 117 of the memory 2 with each other, and sequentially detects the present value as a new second minimum value when the present value is larger than the first minimum value and smaller than the second minimum value. As an initial value of the second minimum value stored in the second value holding (storage) unit 117, the maximum value (for example, 1023 in the case of performing the sampling by the 10-bit A/D converter) among the values which the pulse wave can take is set. The second minimum value is sequentially updated.

As shown in FIG. 9, the second detection unit 103 starts to detect the second minimum value after a minimum value detection start time period T22 has elapsed from the time t21 when the first detection unit 102 detects the first minimum value y21 or the update unit 108 updates the first minimum value y11. It is recommended that the minimum value detection start time period T22 be set at approximately a half cycle of the assumed pulse wave. The detection of the second minimum value is not started until the minimum value detection start time period T22 elapses. Accordingly, an erroneous detection due to the influence of noise, and the like can be eliminated. In FIG. 9, for example, a value y22 of the pulse wave data detected at a time t12 is set as the second minimum value.

As shown in FIG. 8, in the case where a maximum value update time period T11 (for example, 1.5 second) has elapsed since the update unit 108 updated the first maximum value y11 stored in the first value holding (storage) unit 116 in a state where the first detection unit 102 does not detect the new first maximum value, the update unit 108 assigns the second maximum value y12 stored in the second value holding (storage) unit 117 to the first maximum value y11 stored in the first value holding (storage) unit 116, and thereby updates the first maximum value y11. The maximum value update time period T11 defines the lifetime of the first maximum value y11 stored in the first value holding (storage) unit 116. The maximum value update time period T11 is recommended to have a range in which one cycle of the assumed pulse wave will fit.

As shown in FIG. 9, in the case where a minimum value update time period T21 (for example, 1.5 second) has elapsed since the update unit 108 updated the first minimum value y21 stored in the first value holding (storage) unit 116 in a state where the first detection unit 102 does not detect the new first minimum value, the update unit 108 assigns the second minimum value y22 stored in the second value holding (storage) unit 117 to the first minimum value y21 stored in the first value holding (storage unit 116, and thereby updates the first minimum value y21. The minimum value update time period T21 defines the lifetime of the first minimum value y11 stored in the first value holding (storage) unit 116. The minimum value update time period T21 is recommended to have a range in which one cycle of the assumed pulse wave will fit.

After the update unit 108 assigns the second maximum value y12 to the first maximum value y11 and updates the first maximum value y11, the initialization unit 109 initializes the second maximum value y12 stored in the second value holding (storage) unit 117 so that the second detection unit 103 can detect the new second maximum value in the cycle of the pulse wave data, which is next (adjacent) to the cycle in which the second detection unit 103 has detected the second maximum value y12. It is recommended that an initialized value be set at the minimum value (for example, 0 in the case of performing the sampling by the 10-bit A/D converter) among the values which the pulse wave measured by the pulse wave measuring unit 101 can take.

As shown in FIG. 8, also in the case where a maximum value initialization time period T13 (for example, 1.5 second) has elapsed since the update unit 108 updated the second maximum value y12 stored in the second value holding (storage) unit 117, the initialization unit 109 initializes the second maximum value y12 stored in the second value holding (storage) unit 117. The maximum value initialization time period T13 defines the lifetime of the second maximum value y12 stored in the second value holding (storage) unit 117. The maximum value initialization time period T13 just needs to be set so as to lapse at a time later than the lapse of the maximum value update time period T11.

After the update unit 108 assigns the second maximum value y22 to the second maximum value y22 and updates the first minimum value y21, the initialization unit 109 initializes the second minimum value y22 stored in the second value holding (storage) unit 117 so that the second detection unit 103 can detect the new second minimum value in the cycle of the pulse wave data, which is the next cycle to the cycle in which the second detection unit 103 has detected the second minimum value y22. It is recommended that an initialized value be set at the maximum value (for example, 1023 in the case of performing the sampling by the 10-bit A/D converter) among the values which the pulse wave measured by the pulse wave measuring unit 101 can take.

As shown in FIG. 9, also after a minimum value initialization time period T23 (for example, 1.5 second) has elapsed since the update unit 108 updated the second minimum value y22 stored in the second value holding (storage) unit 117, the initialization unit 109 initializes the second minimum value y22 stored in the second value holding (storage) unit 117. The minimum value initialization time period T23 defines the lifetime of the second minimum value y22 stored in the second value holding (storage) unit 117. The minimum value initialization time period T23 just needs to be set so as to lapse at a time later than the elapsed time of the minimum value update time period T21.

Figure 10:
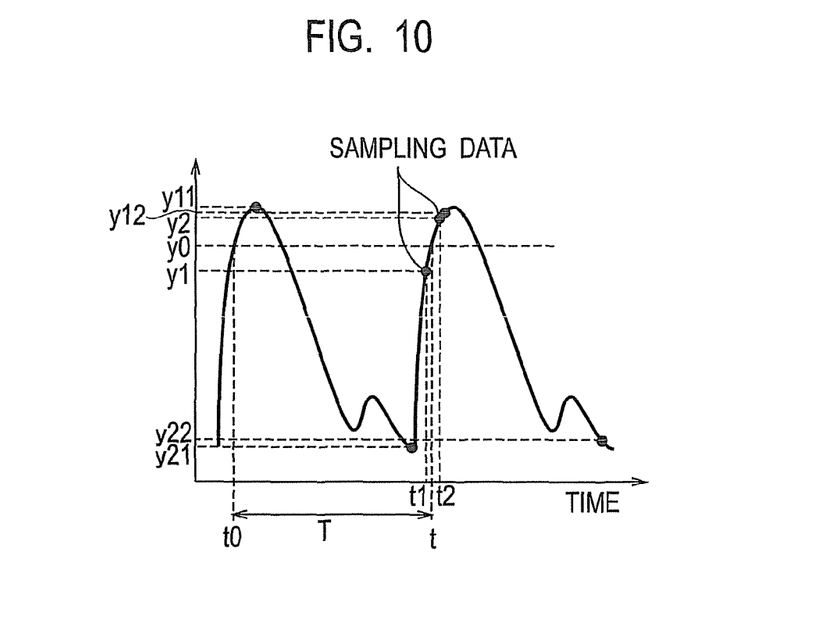
FIG. 10 is a graph for explaining of a calculation processing of a pulse wave interval in a pulse wave measuring method according to the embodiment of the present invention.

As shown in FIG. 10, the threshold value calculation unit 105 calculates a threshold value y0 of the pulse wave data by using the first maximum value y11 stored in the first value holding (storage) unit 116 and the first minimum value y21 stored by the second value holding (storage) unit 117. In FIG. 10, the threshold value y0 is set on the side of the first maximum value y11; however, according to a feature of the pulse wave (affected also by an amplifier and a filter) measured by the pulse wave measuring unit 101, the threshold value y0 may be set at a midpoint between the first maximum value y11 and the first minimum value y21, a value biased from the midpoint to the first maximum value y11 side, a value biased from the midpoint to the first minimum value y21 side, or the like. As shown in FIG. 10, in the case a large upward waveform is observed, it is recommended that the threshold value y0 be set on the first maximum value y11 side.

In FIG. 10, though a value y1 of the pulse wave data does not exceed the threshold value y0 at the sampling time t1, a value y2 of the pulse wave data exceeds the threshold value y0 at the next sampling time t2. The timing detection unit 106 sequentially detects timing when each value of the pulse wave data intersects the threshold value y0 for each cycle. Note that, since the value of the pulse wave data actually intersects the threshold value y0 between the sampling time t1 immediately before exceeding the threshold value y0 and the sampling time t2 immediately after exceeding the threshold value y0, the timing t is calculated by an expression (1) in the case where the value of the pulse wave data in the event of crossing the actual threshold value y0 and present time when the value of the pulse wave data crosses the threshold value y0 are defined as y0 and t, respectively.

$$t = t1 + (t2-t1) \times (y0-y1)/(y2-y1) \quad (1)$$

Hence, when the timing at the previous time and the timing at present time, which are sequentially detected by the timing detection unit 106, are defined as t0 and t, respectively, the interval calculation unit 107 calculates a pulse wave interval T by an expression (2).

$$T = t - t0 \quad (2)$$

The communication unit 110 transmits data of the pulse wave interval T to an external information terminal. As the communication unit 110, for example, a wireless communication function, such as Bluetooth (registered trademark), may be used.

The memory 2 includes a setting time storage unit 115, the first value holding (storage) unit 116 and the second value holding (storage) unit 117. The setting time storage unit 115 pre-stores the maximum value update time period T11, the maximum value detection start time period T12, the maximum value initialization time period T13, the minimum value update time period T21, the minimum value detection start time period T22, and the minimum value initialization time period T23. The first value holding (storage) unit 116 stores the first maximum value and the first minimum value, which are detected by the first detection unit 102 or updated by the update unit 108. The second value holding (storage) unit 117 stores the second maximum value and the second minimum value, which are detected by the second detection unit 103 or updated by the update unit 108.

A semiconductor memory, a magnetic disk, an optical disk, a magneto-optical disk, a magnetic tape or the like may be used for the memory 2. For the semiconductor memory, a read-only memory (ROM) and random-access memory (RAM) may be used. The ROM stores a program executed by the CPU 1 (the details of the program are described later). The RAM serves as a temporary data memory for storing data used in executing a program by the CPU 1, and used as a working domain.

(Pulse Wave Measuring Method)

Figure 11:
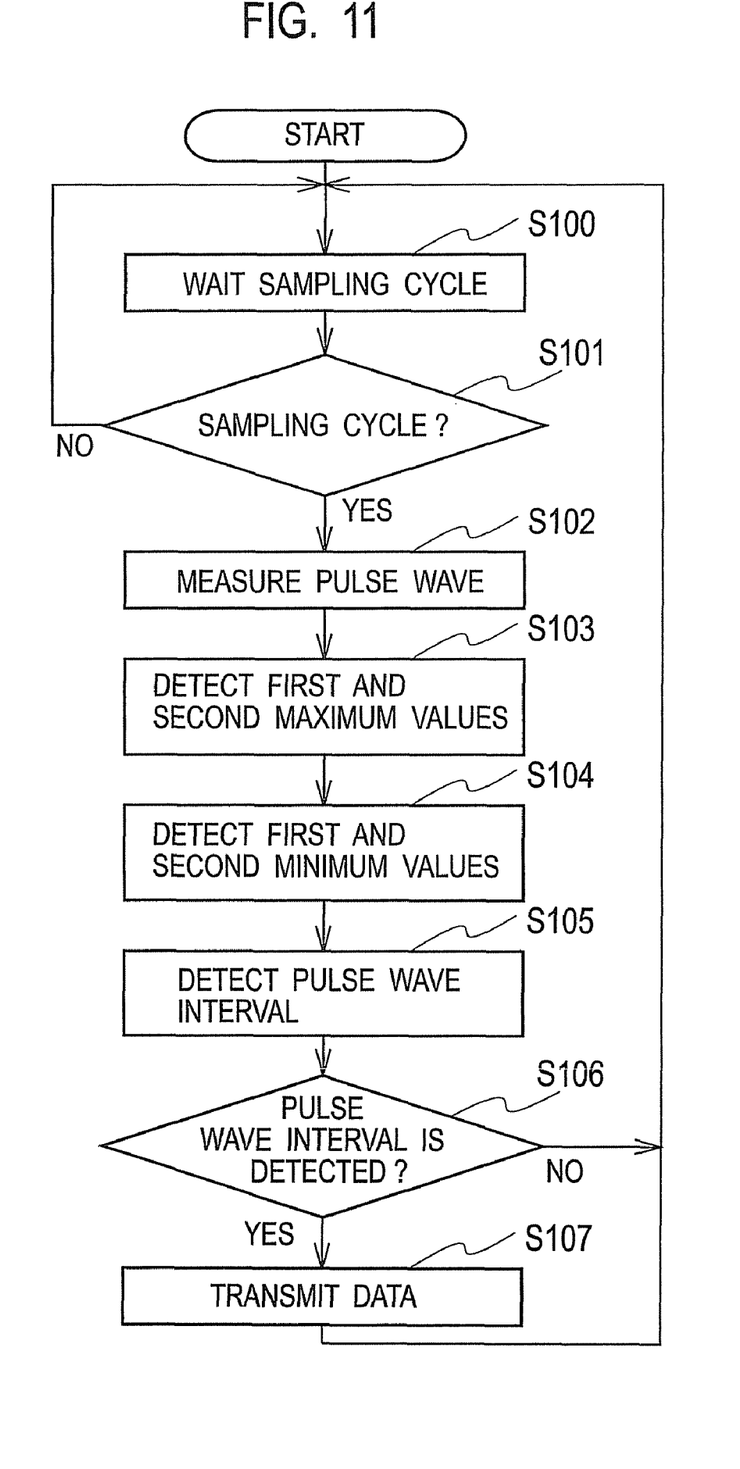
FIG. 11 is a flowchart for explaining an example of the pulse wave measuring method according to the embodiment of the present invention.

Next, a description is made of a pulse wave measuring method according to the embodiment of the present invention while referring to a flowchart of FIG. 11.

In Step S100, upon starting the measurement, the pulse wave measuring apparatus 100 waits for a preset sampling cycle (for example, 50 milliseconds). When the sampling cycle starts in Step S101, the pulse wave measuring unit 101 measures the pulse wave in Step S102.

In Step S103, detection processing for the first and second maximum values is performed. Details of the detection processing for the first and second maximum values are shown in a flowchart of FIG. 12. In the detection processing for the first and second maximum values, in Step S110, the first detection unit 102 determines whether the present value of the pulse wave data measured by the pulse wave measuring unit 101 is larger than the first maximum value y11 stored in the first value holding (storage) unit 102. When the present value is larger than the first maximum value y11, in the Step S111, the update unit 108 assigns the present value to the first maximum value y11 stored in the first value holding (storage) unit 116, and thereby updates the first maximum value y11. The processing then proceeds to detection processing for the first and second minimum values.

Figure 12:
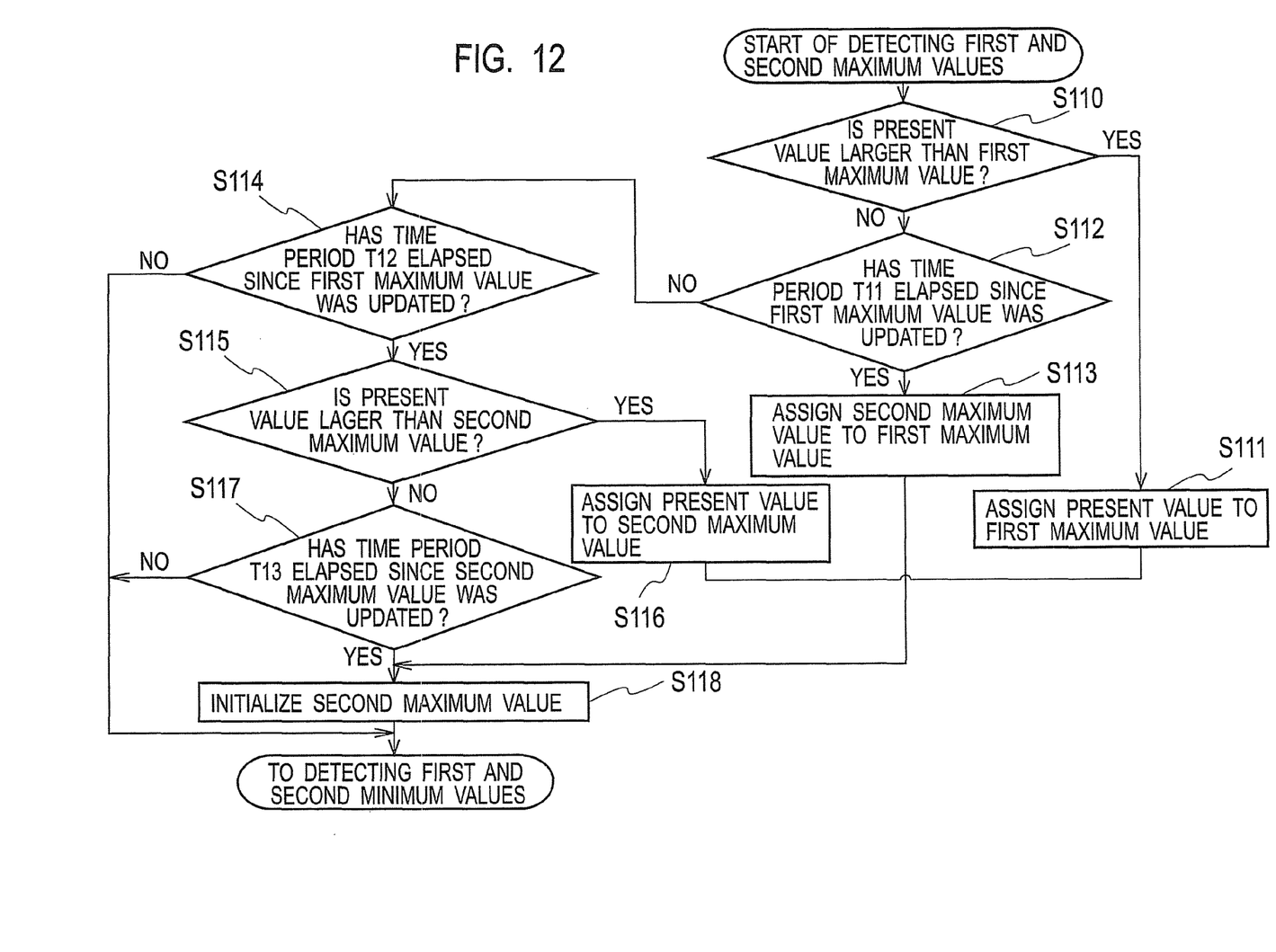
FIG. 12 is a flowchart for explaining the example of first and second maximum values detection processing in the pulse wave measuring method according to the embodiment of the present invention.

When the present value is not larger than the first maximum value y11 stored in the first value holding (storage) unit 116 in Step S110, in Step S112, based on a time period measured by the time period measuring unit 104, it is determined whether or not the maximum value update time period T11 (for example, 1.5 second) has elapsed since the first maximum value y11 was updated. In the case where the maximum value update time period T11 has elapsed, then in Step S113, the update unit 108 assigns the second maximum value y12 stored in the second value holding (storage) unit 117 to the first maximum value y11 stored in the first value holding (storage) unit 116, and thereby updates the first maximum value y11. Thereafter, in Step S118, the initialization unit 109 initializes the second maximum value y12 stored in the second value holding (storage) unit 117. Since the second maximum value y12 is initialized once, the second detection unit 103 can detect the new second maximum value in the next cycle of the pulse wave data.

In the case where the maximum value update time period T11 has not elapsed in Step S112, then in Step S114, based on the time period measured by the time period measuring unit 104, it is determined whether or not the maximum value detection start time period T12 (for example, 1.5 second) has elapsed since the first maximum value y11 was updated. In the case where the maximum value detection start time period T12 has elapsed, then in Step S115, the second detection unit 103 determines whether the present value is larger than the second maximum value y12. In the case where the present value is larger than the second maximum value y12, then in Step S116, the update unit 108 assigns the present value to the second maximum value y12 stored in the second value holding (storage) unit 117, and thereby updates the second maximum value y12. The processing then proceeds to detection processing for the first and second minimum values.

In the case where the present value is not larger than the second maximum value y12 in Step S115 then, in Step S117, based on the time period measured by the time period measuring unit 104, it is determined whether or not the maximum value initialization time period T13 (for example, 1.5 second) has elapsed since the second maximum value y12 was updated. In the case where the maximum value initialization time period T13 has elapsed, in Step S118, the initialization unit 109 initializes the second maximum value y12 stored in the second value holding (storage) unit 117. Since the second maximum value y12 is initialized once, the second detection unit 103 can detect the new second maximum value in the next cycle of the pulse wave data.

In Step S104, the detection processing for the first and second minimum values is performed. Details of the detection processing for the first and second minimum values are shown in a flowchart of FIG. 13. In the detection of the processing for the first and second minimum values, in Step S120, the first detection unit 102 determines whether the pulse wave data measured by the pulse wave measuring unit 101 is smaller than the first minimum value y21. In the case where such a present value is smaller than the first minimum value y21, in Step S121, the update unit 108 assigns the present value to the first minimum value y21 stored in the second value holding (storage) unit 117, and thereby updates the first minimum value y21. Then, the processing proceeds to detection processing for the pulse wave interval. In the case where the present value is not smaller than the first minimum value y21 in Step S120, the processing proceeds to Step S122.

Figure 13:
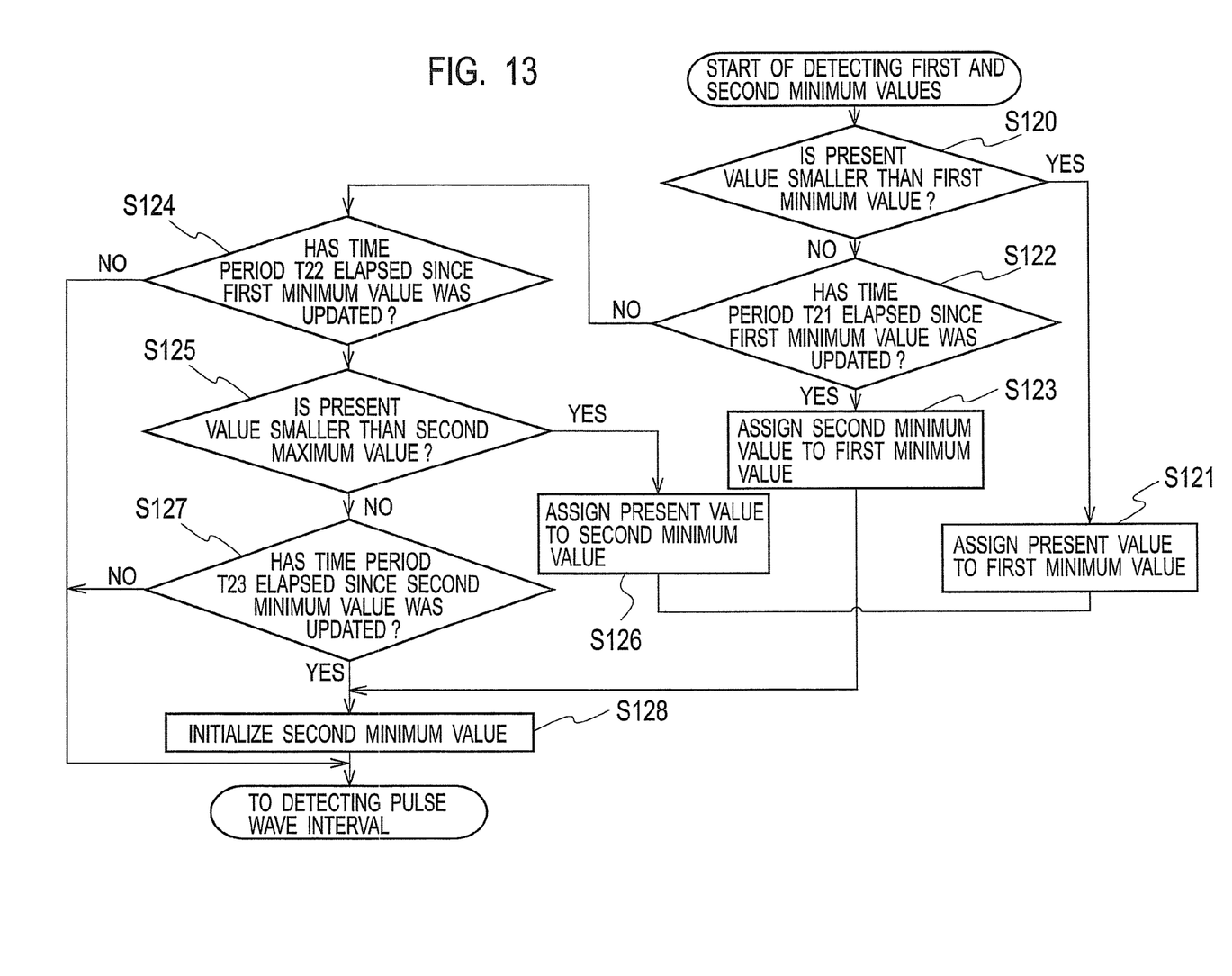
FIG. 13 is a flowchart for explaining the example of first and second minimum values detection processing in the pulse wave measuring method according to the embodiment of the present invention.

In Step S122, based on the time period measured by the time period measuring unit 104, it is determined whether or not the minimum value update time period T21 (for example, 1.5 second) has elapsed since the first minimum value y21 was updated. In the case where the minimum value update time period T21 has elapsed, in Step S123, the update unit 108 assigns the second minimum value y22 to the first minimum value y21, and thereby updates the first minimum value y21. Thereafter, in Step S128, the initialization unit 109 initializes the second minimum value y22 stored in the second value holding (storage) unit 117. Since the second minimum value y22 is initialized once, the second detection unit 103 can detect the new second minimum value in the next cycle of the pulse wave data, and can store the new second minimum value in the second value holding (storage) unit 117. In the case where the minimum value update time period T21 has not elapsed in Step S122, the processing proceeds to Step S124.

In Step S124, based on the time period measured by the time period measuring unit 104, it is determined whether or not the minimum value detection start time period T22 (for example, 0.5 second) has elapsed since the first minimum value y21 was updated. In the case where the minimum value detection start time period T22 has elapsed, in Step S125, the second detection unit 103 determines whether the present value is smaller than the second minimum value y22. In the case where the present value is smaller than the second minimum value y22, in Step S126, the update unit 108 assigns the present value to the second minimum value y22, and thereby updates the second maximum value y22. The processing then proceeds to the detection processing for the first and second minimum values. The processing proceeds to Step S127 where the present value is not smaller than the second minimum value y22.

In Step S127, based on the time period measured by the time period measuring unit 104, it is determined whether or not the minimum value initialization time period T23 (for example, 1.5 second) has elapsed since the second minimum value y22 was updated. In the case where the minimum value initialization time period T23 has elapsed, in Step S128, the initialization unit 109 initializes the second minimum value y22 stored in the second value holding (storage) unit 117. Since the second minimum value y22 is initialized once, the second detection unit 103 can detect the new second minimum value in the next cycle of the pulse wave data, and can store the new second minimum value in the second value holding (storage) unit 117.

In Step S105, the detection processing for the pulse wave interval is performed. First, the threshold value calculation unit 105 sets the threshold value y0 by using the first maximum value y11 and the first minimum value y21, which are stored in the first value holding (storage) unit 116. In two continuous cycles, by using the expression (1), the timing detection unit 106 sequentially detects the timings t when the measured pulse wave data intersects the threshold value y0. The interval calculation unit 107 calculates the pulse wave interval T by the expression (2) by using the previous timing t0 and the timing t, which are detected by the timing detection unit 106.

In Step S106, it is determined whether or not the timing detection unit 106 detects the timings t and the interval calculation unit 107 calculates the pulse wave interval T. In the case where the timing detection unit 106 detects the timings t and the interval calculation unit 107 calculates the pulse wave interval T, then in Step S107, the communication unit 110 transmits the data of the pulse wave interval T and the like to the external information terminal.

In accordance with the pulse wave measuring apparatus 100 and the pulse wave measuring method according to the embodiment of the present invention, when calculating the pulse wave interval T while taking as a reference the threshold value y0 obtained by using the first maximum value y11 and the first minimum value y21 in the predetermined section, in order to obtain the first maximum value y11 and the first minimum value y21, the pulse wave data for each sampling cycle (for example, 50 milliseconds) in the predetermined section (for example, 1.5 second) is not entirely stored. However, the first maximum value y11, the first minimum value y21, the second maximum value y12 and the second minimum value y22 are sequentially updated, whereby the first maximum value y11, the first minimum value y21, the second maximum value y12 and the second minimum value y22, are stored. In such a way, it is possible to detect the pulse wave interval T with an accuracy equal to that of the conventional method. Hence, even an MPU that has restricted sampling frequency and memory capacity is capable of measuring the pulse wave interval highly accurately.

(Program)

The series of procedures shown in FIG. 11 can be achieved by controlling the pulse wave measuring apparatus 100 shown in FIG. 1 by means of a program having an algorism equivalent to that of FIG. 11. The procedures shown in FIG. 11 include: the step of measuring the pulse wave data; the step of individually detecting the first maximum value y11 and the first minimum value y21 from the pulse wave data, periodically and sequentially; the step of detecting the second maximum value y12, which is the next largest to the first maximum value y11, and the second minimum value y22, which is the next smallest to the first minimum value y21, from the pulse wave data, periodically and sequentially; the step of, after elapse of the maximum value update time period T11 after the update of the first maximum value y11, assigning the second maximum value y12 to the first maximum value y11 stored in the first value holding (storage) unit 116, and updating the first maximum value y11; the step of, after elapse of the minimum value update time period T21 after the update of the first minimum value y21, assigning the second minimum value y22 to the first minimum value y21 stored in the second value holding (storage) unit 117, and updating the first minimum value y21; the step of, after the update of the first maximum value y11, initializing the second maximum value y12 stored in the second value holding unit 117 so that the new second maximum value y12 can be detected in the next cycle of the pulse wave data, in which the second maximum value y12 is detected; the step of, after the update of the first minimum value y21, initializing the second minimum value y22 stored in the second value holding (storage) unit 117 so that the new second minimum value y22 can be detected in the next cycle of the pulse wave data, in which the second minimum value y22 is detected; the step of calculating the threshold value y0 by using the first maximum value y11 and the first minimum value y21, which are stored in the first value holding (storage) unit 116; the step of detecting the timing t and t0 at which the pulse wave data intersects the threshold value y0 in the continuous two cycles; and the step of calculating the pulse wave interval T from the timings t and t0.

The program may be stored in the memory 2 of the pulse wave measuring apparatus 100 according to the embodiment of the present invention. The program can be stored in a computer-readable storage medium. The procedures of the method according to the embodiment of the present invention can be performed by reading the program from the computer-readable storage medium to the data memory 2.

Here, the "computer-readable storage medium" means any media and the like that can store a program include, e.g., external memory units, semiconductor memories, magnetic disks, optical disks, magneto-optical disks, magnetic tape, and the like for a computer. To be more specific, the "computer-readable storage media" include flexible disks, CD-ROMs, MO disks, cassette tape, open reel tape, and the like. For example, the main body of the mask data generation system can be configured to incorporate a flexible disk drive and an optical disk drive, or to be externally connected thereto.

Other Embodiment

Various modifications will become possible for those skilled in the art after receiving the teachings of the present disclosure without departing from the scope thereof.

The maximum value update time period T11, the minimum value update time period T21, the maximum value initialization time period T13 and the minimum value initialization time period T23 may be preset, or may be dynamically changed based on the pulse wave interval T at the previous time, for example, may be set at 1.5 times the pulse wave interval T.

The maximum value detection start time period T12 and the minimum value detection start time period T22 may be preset, or may be dynamically changed based on the data of the pulse wave interval T and the like.

Although the data is transmitted to the external information terminal every time when the pulse wave interval T is detected, if the pulse wave measuring apparatus 100 includes a flash memory or the like, then the data may be recorded in the flash memory or the like without being transmitted. Alternatively, if the pulse wave measuring apparatus 100 includes a display unit such as a liquid crystal display, the data may be displayed on the display unit.

What is claimed is:

1. A pulse wave measuring apparatus comprising:
 a pulse wave measuring unit configured to measure pulse wave data;
 a first detection unit configured to detect first maximum values and first minimum values from the pulse wave data, and store the first maximum values and the first minimum values in a first value storage unit, respectively;
 a second detection unit configured to detect second maximum values and second minimum values from the pulse wave data sequentially, and to store the second maximum values and the second minimum values in a second value storage unit, wherein the second maximum values are the next largest values in amplitude relative to the first maximum values, the second minimum values are the next smallest values in amplitude relative to the first minimum values;
 an update unit configured to update the first maximum value stored in the first value storage unit with the second maximum value after elapse of a maximum value update time period after updating the last first maximum value, and to update the first minimum value stored in the first value storage unit with the second minimum value after elapse of a minimum value update time period after updating the last first minimum value;
 an initialization unit configured to initialize the second value storage unit so that a new second maximum value can be stored in a next cycle of the pulse wave data, in which the last second maximum value is detected, after updating the last first maximum value, and to initialize the second value storage unit so that a new second minimum value can be stored in a next cycle of the pulse wave data, in which the last second minimum value is detected, after updating the last first minimum value;

a timing detection unit configured to detect a timing, at which the pulse wave data intersects a threshold value determined by the last first maximum value and the last first minimum value in two continuous cycles; and an interval calculation unit configured to calculate a pulse wave interval using the last timing and the present timing detected by the timing detection unit, wherein detection of the second maximum values by the second detection unit is performed by detecting a present value of the pulse wave data as a new second maximum value when the present value is smaller than the last first maximum value and larger than the last second maximum value, and detection of the second minimum values by the second detection unit is performed by detecting the present value as a new second minimum value when the present value is larger than the last first minimum value and smaller than the last second minimum value.

2. The apparatus of claim 1, wherein detection of the first maximum values by the first detection unit is performed by detecting a present value of the pulse wave data as the new first maximum value when the present value is larger than the last first maximum value, and detection of the first minimum values by the first detection unit is performed by detecting the present value as the new first minimum value when the present value is smaller than the last first minimum value.

3. The apparatus of claim 1, wherein detection of the second maximum values by the second detection unit is performed by starting detection of the new second maximum value after the elapse of a maximum value detection start time period after updating the last first maximum value; and detection of the second minimum values by the second detection unit is performed by starting detecting the new second minimum value after a minimum value detection start time period after updating the last first minimum value.

4. The apparatus of claim 1, wherein the initialization of the second value storage unit so that the new second maximum value can be stored by the initialization unit is performed by initializing the last second maximum value after the elapse of a maximum value initialization time period after updating the last second maximum value; and initialization of the second value storage unit so that the new second minimum value can be stored by the initialization unit is performed by initializing the last second minimum value after the elapse of a minimum value initialization time period after updating the last second minimum value.

5. The apparatus of claim 1, further comprising: a communication unit configured to transmit the pulse wave interval to an external terminal.

6. A method for measuring a pulse wave, comprising:
using a computer to perform the steps of:
detecting first maximum values and first minimum values from data of the pulse wave, respectively and sequentially, and storing the first maximum values and the first minimum values in a first value storage unit;

detecting second maximum values and second minimum values from the pulse wave data, and storing the second maximum values and the second minimum values to a first value storage unit, respectively, wherein the second maximum values are the next largest values in amplitude relative to the first maximum values, the second minimum values are the next smallest values in amplitude relative to the first minimum values;

updating the first maximum value stored in the first value storage unit with the second maximum value after a maximum value update time period has elapsed after updating the last first maximum value;

updating the first minimum value stored in the first value storage unit with the second minimum value after a minimum value update time period has elapsed after updating the last first minimum value;

initializing the second value storage unit so that a new second maximum value can be stored in the next cycle of the pulse wave data, in which the last second maximum value is detected, after updating the last first maximum value;

initializing the second value storage unit so that a new second minimum value can be stored in the next cycle of the pulse wave data, in which the last second minimum value is detected, after updating the last first minimum value;

detecting timing, at which the pulse wave data intersects a threshold value determined by using the last first maximum value and the last first minimum value in two continuous cycles; and calculating a pulse wave interval using the last timing and the present timing, wherein detecting the second maximum value and the second minimum value comprises:

detecting the present value as a new second maximum value when the present value is smaller than the last first maximum value and larger than the last second maximum value; and detecting the present value as a new second minimum value sequentially when the present value is larger than the last first minimum value and smaller than the last second minimum value.

7. The method of claim 6, wherein detecting the first maximum values and the first minimum values comprises:
detecting a present value of the pulse wave data as a new first maximum value when the present value is larger than the last first maximum value; and
detecting the present value as a new first minimum value when the present value is smaller than the last first minimum value.

8. The method of claim 6, wherein detecting the second maximum value and the second minimum value respectively comprises:
starting detection of the new second maximum value after a maximum value detection start time period has elapsed after updating the last first maximum value; and
starting detecting the new second minimum value after a minimum value detection start time period has elapsed after updating the last first minimum value.

9. The method of claim 6, wherein
initializing the second value storage unit after updating the present first maximum value comprises: initializing the last second maximum value after a maximum value initialization time period has elapsed after updating the last second maximum value; and
initializing the second value storage unit after updating the present first maximum value comprises: initializing the last second minimum value after a minimum value initialization time period has elapsed after updating the last second minimum value.

10. The method of claim 6, further comprising: transmitting the pulse wave interval to an external terminal.

* * * * *